(12) United States Patent
DesJardins et al.

(10) Patent No.: US 10,244,818 B2
(45) Date of Patent: Apr. 2, 2019

(54) VARIABLE HARDNESS ORTHOTIC

(71) Applicant: CLEMSON UNIVERSITY, Clemson, SC (US)

(72) Inventors: John DesJardins, Clemson, SC (US); Scott Edward Stanley, Indianapolis, IN (US); Breanne Przestrzelski, Swannanoa, NC (US); Timothy C. Pruett, Central, SC (US); Steve L. Hoeffner, Easley, SC (US); Brian Daryl Kaluf, Greenville, SC (US)

(73) Assignees: Clemson University Research Foundation, Clemson, SC (US); Ability Prosthetics & Orthotics, Inc., Greenville, SC (US)

( * ) Notice: Subject to any disclaimer, the term of this patent is extended or adjusted under 35 U.S.C. 154(b) by 58 days.

(21) Appl. No.: 15/046,661

(22) Filed: Feb. 18, 2016

(65) Prior Publication Data

US 2016/0235158 A1     Aug. 18, 2016

Related U.S. Application Data

(60) Provisional application No. 62/117,690, filed on Feb. 18, 2015.

(51) Int. Cl.
*A43B 13/20*     (2006.01)
*A43B 7/28*      (2006.01)
(Continued)

(52) U.S. Cl.
CPC .............. *A43B 7/28* (2013.01); *A43B 1/0009* (2013.01); *A43B 13/20* (2013.01); *A43B 17/006* (2013.01);
(Continued)

(58) Field of Classification Search
CPC ..... A43B 1/0009; A43B 17/006; A43B 17/02; A43B 17/03; A43B 13/20
See application file for complete search history.

(56) References Cited

U.S. PATENT DOCUMENTS

| | | | | |
|---|---|---|---|---|
| 532,429 | A | * | 1/1895 | Rogers ................. A43B 13/181 36/140 |
| 4,130,948 | A | | 12/1978 | Krug |

(Continued)

FOREIGN PATENT DOCUMENTS

| | | |
|---|---|---|
| EP | 2196173 | 6/2010 |
| EP | 2359288 | 8/2011 |

(Continued)

OTHER PUBLICATIONS

Dombroski, et al.; "The use of a low cost 3D scanning and printing tool in the manufacture of custom-made foot orthoses: a preliminary study," *BMC Research Notes* 2014, 7:443 (4 pages) (http://www.biomedcentral.com/1756-0500/7/443).

(Continued)

*Primary Examiner* — Ted Kavanaugh
(74) *Attorney, Agent, or Firm* — Dority & Manning, PA

(57) ABSTRACT

Orthotics and methods for forming orthotics are described. The orthotics can be designed with a patient-specific design and can include variation in hardness across the orthotic so as to satisfy clinical need. An orthotic can be a custom-designed orthotic formed according to an additive manufacturing process such as a 3-D printing methodology. Through utilization of on-site formation methods such as 3-D printing, an orthotic can be designed, formed and fit at the point of care in a much shorter time period than traditional orthotics. The orthotics can include a layer that includes a plurality of cells across the layer. The layer can exhibit variable hardness across the layer through variation in cell (Continued)

void volume and optionally material of formation across the layer.

18 Claims, 4 Drawing Sheets

(51) Int. Cl.
  *A43B 17/00* (2006.01)
  *A43B 17/02* (2006.01)
  *A61F 5/01* (2006.01)
  *A43B 17/03* (2006.01)
  *A43B 1/00* (2006.01)
  *B33Y 10/00* (2015.01)

(52) U.S. Cl.
  CPC .............. *A43B 17/02* (2013.01); *A43B 17/03* (2013.01); *A61F 5/0111* (2013.01); *B33Y 10/00* (2014.12)

(56) References Cited

U.S. PATENT DOCUMENTS

| | | | |
|---|---|---|---|
| 4,464,850 A | | 8/1984 | Ebert et al. |
| 4,485,568 A | * | 12/1984 | Landi .................. A43B 1/0009 |
| | | | 36/103 |
| 4,979,252 A | | 12/1990 | Daley |
| 5,174,049 A | * | 12/1992 | Flemming ............ A43B 1/0009 |
| | | | 36/28 |
| 5,201,125 A | * | 4/1993 | Shorten ................ A43B 1/0009 |
| | | | 36/28 |
| 7,322,950 B2 | | 1/2008 | Modglin |
| 7,380,352 B2 | | 6/2008 | Seiter |
| 7,506,459 B2 | | 3/2009 | Grisoni et al. |
| 8,538,570 B2 | | 9/2013 | Stanhope et al. |
| 8,565,909 B2 | | 10/2013 | Bickel et al. |
| 8,583,272 B2 | | 11/2013 | Spector |
| 9,020,626 B2 | | 4/2015 | Spector |
| 2004/0159013 A1 | * | 8/2004 | Ganon .................... A43B 9/06 |
| | | | 36/25 R |
| 2004/0194352 A1 | | 10/2004 | Campbell et al. |
| 2013/0104422 A1 | * | 5/2013 | Hatfield ................. A43B 5/001 |
| | | | 36/103 |
| 2014/0120319 A1 | | 5/2014 | Joseph |
| 2015/0237959 A1 | * | 8/2015 | Wynn .................... A43B 7/142 |
| | | | 36/44 |
| 2016/0037860 A1 | * | 2/2016 | Holt ..................... A43B 13/186 |
| | | | 36/28 |

FOREIGN PATENT DOCUMENTS

| | | |
|---|---|---|
| EP | 2589311 | 5/2013 |
| EP | 2708211 | 3/2014 |
| WO | WO 2003/015558 | 2/2003 |
| WO | WO 2014/014977 | 1/2014 |
| WO | WO 2014/080217 | 5/2014 |

OTHER PUBLICATIONS

Solescience Website; http://www.solescience.ca/custom-foot-orthoses/ ; accessed Jul. 21, 2016 (7 pages).
Bus, et al. Pressure Relief and load redistribution by custom-made insoles in diabetic patients with neuropathy and foot deformity. *Clinical Biomechanics*, 19 (2004), pp. 629-638.
Frykberg, et al. Diabetic foot disorders: a clinical practice guideline. *Journal of Foot and Ankle Surgery*, 45 (5 Suppl) (2006), pp. S1-S66.
Lott, et al. Pressure gradient and subsurface shear stress on the neuropathic foot. *Clinical Biomechanics*, 23 (2008), pp. 342-348.
Paton, et al. Effectiveness of insoles used for the prevention of ulceration in the neuropathic diabetic foot: a systematic review. *Journal of Diabetes and Its Complications*, 25 (2011), pp. 52-62.
Reiber, et al. Lower extremity foot ulcers and amputations in diabetes. *Diabetes in America*, 95(1498), (1995), pp. 409-428.
Stocki, et al. Costs of lower-extremity ulcers among patients with diabetes. *Diabetes Care*, 27(9), (2004), pp. 2129-2134.
Veves, et al. The risk of foot ulceration in diabetic patients with high foot pressure: a prospective study, *Diabetologia*, 35, (1992), pp. 660-663.

* cited by examiner

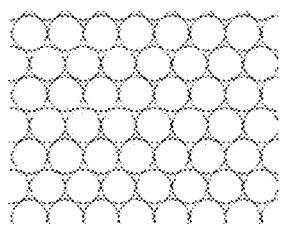
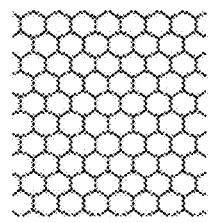
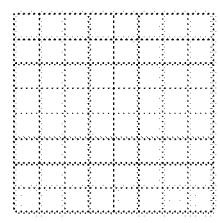
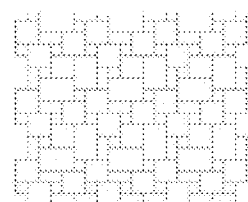
FIG. 4  FIG. 5  FIG. 6  FIG. 7
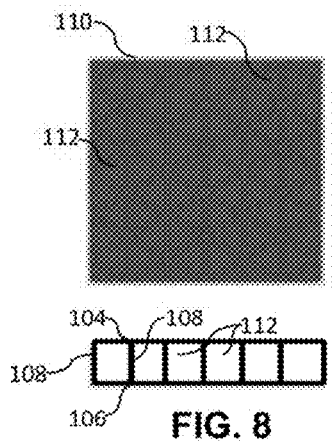
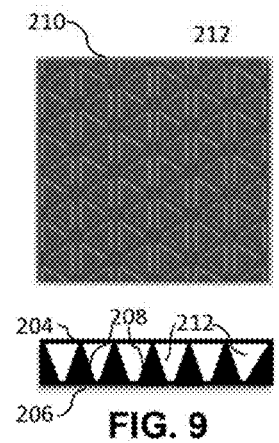
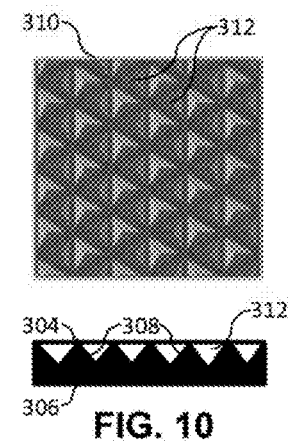
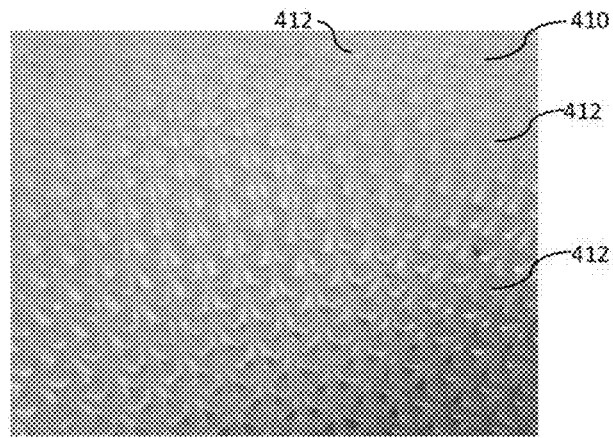
FIG. 8  FIG. 9  FIG. 10
FIG. 11

VARIABLE HARDNESS ORTHOTIC

CROSS REFERENCE TO RELATED APPLICATION

The present application claims priority to U.S. Provisional Patent Application Ser. No. 62/117,690 titled "3D Printed Variable Hardness Foot Orthotics" of DesJardins, et al. filed on Feb. 18, 2015, the disclosure of which is incorporated by reference herein.

BACKGROUND

Orthotics are generally considered to encompass any device that provides external biomechanic support to a human or animal body surface. For example, a foot orthotic generally takes the form of a partial or full insole for a shoe. An orthotic can include regions of support and/or relief for location between the skin/body of a subject and an environmental interface, e.g., a shoe sole. A region of support is generally designed to support weight-bearing regions of the subject and/or to provide correct positioning of a body region (e.g., the foot). A region of relief may be a softer, less-stiff region and is designed to off-load or distribute weight-bearing forces of specific regions of a subject's body so as to affect pressure in that local area, for instance to reduce pain and encourage wound healing. An orthotic may be used to support a region post-surgery, to improve gait of a user (in the case of a foot or leg orthotic), to provide relief from conditions such as ulcers, bony abnormalities, etc.

Foot ulcers affect up to 25% of all diabetics (estimated at over 25 million in the US as of 2015), and are a major national health concern given the growing diabetic population. Left untreated, foot ulcers can lead to loss of lower limb function and even amputation. In fact, approximately 85% of all lower limb amputations are preceded by a non-healing foot ulcer. Recent clinical research supports the use of orthotic shoe inserts to alter pressure conditions at foot ulcers. While traditional pressure-offloading foot orthotics can be effective in reducing ulceration and relieving pain, clinical prescription and design of these orthotics remains qualitative, and clinicians continue to struggle with accurate, effective, and repeatable methods to design foot orthotics that can affect pressure at the area of foot ulcers. Overall orthotic shape is usually satisfactory, but targeting of ulcer offloading accurately is geometrically and spatially imprecise, with correlation between the ulcer area and the offloading area often differing by 1 to 3 square centimeters (cm²). For example, FIG. 1 is a pressure heat map of a foot imprint showing a simulated area 1 of interest (e.g., a wound or ulcer) in the foot. In traditional orthotic formation, the offloading area, which ideally will encompass the area 1 as well as a portion of the surrounding area, will not take into account the pressure gradients and areas of the wound, leading to a qualitative prescription and the outcome of pressure reduction in the weight bearing regions including portions of the would itself.

In addition to design limitations, prolonged manufacturing times with existing fabrication methods reduce patient follow-up and compliance, thus impacting clinical outcomes. For instance, the current orthotic manufacturing cycle includes a shape capture of a region, e.g., a patient's foot, generally by taking an impression or a scan of the region, and the orthotic is then developed using manual techniques—optionally with the aid of software. The primary cushioning layer of a foot orthotic is generally fabricated from layering of multiple foam sheet materials followed by adhesion and vacuum forming over a model of the patient's anatomy, to create the custom shape of the orthotic with any additional base, cushioning or cover layers. Offloading regions may be machined as a recess in the sheet material and a less hard material positioned and attached in the recess. The entire process is time consuming (e.g., up to 2 weeks elapsed time), expensive (up to $250 per insert), off-site, inconsistent (difficult to recreate the same embodiment) and highly dependent on fabricator skill. Moreover, multiple office visits are often required due to multiple steps in the process and also adjustments for improper fit, particularly as the wound characteristics change over time, with few quantifiable metrics for assessment of effective offloading over time, leading to low patient compliance. In addition, the traditional fabrication method can lead to sharp boundaries between weight-bearing and offloading areas of the orthotic, which can further irritate wound areas and lead to increased pain, poor patient compliance, and slower healing.

What are needed in the art are improved orthotic materials and designs as well as a clinician-to-patient manufacturing cycle that can be utilized to produce the improved foot orthotics. For example, it would be useful to provide a custom-fit foot orthotic in reduced time through utilization of low cost, on-site manufacturing processes.

SUMMARY

Objects and advantages of the disclosed subject matter will be set forth in part in the following description, or may be obvious from the description, or may be learned through practice of the invention.

According one embodiment, disclosed is an orthotic layer that exhibits a variable hardness across the layer. More specifically, the layer can include a plurality of cells across the layer that are arranged in a predetermined pattern and a single non-overlapping stratum across the layer. A first portion of the cells in a first region of the layer can each define a first void volume and a second portion of the cells in a second region of the layer can each define a second void volume. As such, the first region can have a first hardness and the second region can have a second, different hardness as determined according to ASTM D 2240-05. In one embodiment, the orthotic can be a foot orthotic.

According to another embodiment disclosed is an orthotic that includes a cushion layer that includes a plurality of cells across the layer. A first portion of the cells in a first region of the cushion layer can each define a first void volume and a second portion of the cells in a second region of the cushion layer can each define a second void volume. As such, the first region can have a first hardness and the second region can have a second, different hardness as determined according to ASTM D 2240-05. An orthotic can include additional layers. For instance, in one embodiment, the orthotic can include the cushion layer in conjunction with a base layer adjacent to the bottom side of the cushion layer and/or can include a top layer adjacent to the upper side of the cushion layer. In one particular embodiment, the orthotic can be a foot orthotic Also disclosed is a method for forming a custom-made orthotic. For instance, a method can include determining one or more characteristics of a portion of a subject's anatomy (e.g., a foot) and forming at least one layer of the orthotic based upon the characteristic(s). In particular, first and second regions of the layer can be formed based upon desired areas of load-bearing and pressure off-loading for the subject. The method can optionally include forming one or more additional layers of the orthotic and locating the layers adjacent to one another. According to one embodiment, one or more layers of the custom-made orthotic can be formed according to an additive manufacturing process such as 3-D printing.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

FIG. 4 presents one embodiment of layer cell geometry.

FIG. 5 presents another embodiment of layer cell geometry.

FIG. 6 presents another embodiment of layer cell geometry.

FIG. 7 presents another embodiment of layer cell geometry.

FIG. 8 presents a top view and a side view of a plurality of cells each having a relatively large void volume.

FIG. 9 presents a top view and a side view of a plurality of cells, each having a smaller void volume as compared to the cells of FIG. 8.

FIG. 10 presents a top view and a side view of a plurality of cells, each having a smaller void volume as compared to the cells of FIG. 8 and FIG. 9.

FIG. 11 is a photograph of a bottom surface of a layer.

DETAILED DESCRIPTION

Figure 1:
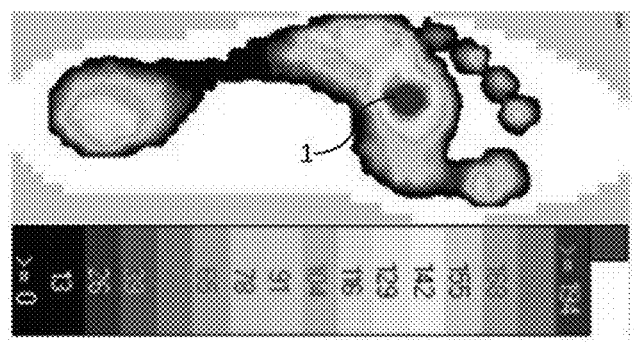
FIG. 1 presents a pressure heat map of a foot including an area of interest and showing different pressure areas of a footstep.

Reference now will be made to embodiments of the disclosed subject matter, one or more examples of which are set forth below. Each example is provided by way of an explanation of the subject matter, not as a limitation thereof. In fact, it will be apparent to those skilled in the art that various modifications and variations can be made without departing from the scope or spirit of the disclosed subject matter. For instance, features illustrated or described as one embodiment can be used on another embodiment to yield still a further embodiment. Thus, it is intended that the present disclosure cover such modifications and variations as come within the scope of the appended claims and their equivalents. It is to be understood by one of ordinary skill in the art that the present discussion is a description of exemplary embodiments only, and is not intended as limiting the broader aspects of the present disclosure.

The present disclosure is generally directed to orthotics and methods for forming orthotics. More specifically, the orthotics can be designed with a patient-specific design and can include variation in hardness across the orthotic so as to satisfy clinical need. As utilized herein, the term "hardness" with respect to an orthotic or orthotic layer is intended to refer to the structural stiffness or indent material hardness equivalent and can be determined according to ASTM D 2240-05.

The presently disclosed orthotics can include materials and material arrangements that can accurately affect pressures and pressure gradients between patient anatomy and pathology and external interfaces such as foot orthotics. For example, disclosed orthotics that can target pressure reduction and pressure gradients across specific anatomical locations of interest.

Disclosed methods and products can be utilized in treatment of a variety of issues including, and without limitation, ulcers such as diabetic ulcers. In one particular embodiment, an orthotic can be a custom-designed orthotic. In one embodiment, an orthotic can be formed according to an additive manufacturing process, and in one particular embodiment a 3-D printing methodology. Through utilization of on-site formation methods such as 3-D printing, an orthotic can be designed, formed and fit at the point of care in a much shorter time period than traditional orthotics.

According to the disclosure, an orthotic can include one or more layers that can include variations in material composition and/or material geometry across the orthotic to provide a variation in hardness across the orthotic. In one particular embodiment, the hardness variation can be according to a custom design for an individual patient and can provide the desired weight-bearing and/or offloading areas with high precision and accuracy. Beneficially, disclosed orthotics can be formed with high repeatability in production and can include hardness gradient precision and design not possible in previous orthotics. The fast formation capability and the ability to form a well-defined hardness gradient on the orthotic can allow for improved treatment response, as a new orthotic can be prepared quickly in response to changes in the subject's anatomical area of interest (e.g., an ulcer). Moreover, a multi-layer orthotic can be updated to better match a subject's changing needs by replacement of only a single layer of the orthotic, which can further improve treatment options for a patient.

While much of the following discussion is directed to foot orthotics, it should be understood that the present disclosure is not intended to be limited to foot orthotics. Orthotics as disclosed herein can be utilized to support and/or cushion any area of a subject's body. In general, an orthotic can be located at any desired area and can be located between the skin and an external element such that pressures on the skin are controlled. The orthotic can thus act to affect pressure between the subject and an external element. Examples of exemplary orthotics can include, but are not limited to, ankle foot orthoses, knee ankle foot orthoses, hip knee ankle foot orthoses, spinal orthoses, wrist orthoses, elbow orthoses, shoulder orthoses, knee cushion systems, hand/palm/grip cushion systems, head/helmet cushion systems, hip/buttocks cushion systems, elbow cushion systems, etc.

An orthotic can include one or more layers across the orthotic. In one embodiment, the orthotic can include a cushion layer as an inner layer that is sandwiched between other layers. For instance, a foot orthotic can include a cushion layer between a shoe sole-contacting base layer and a foot-contacting top layer, optionally with additional layers as well. This arrangement is not a requirement of the disclosure, however, and in some embodiments, the orthotic can be a single layer orthotic, a bilayer orthotic or a multi-layer orthotic.

Figure 2:
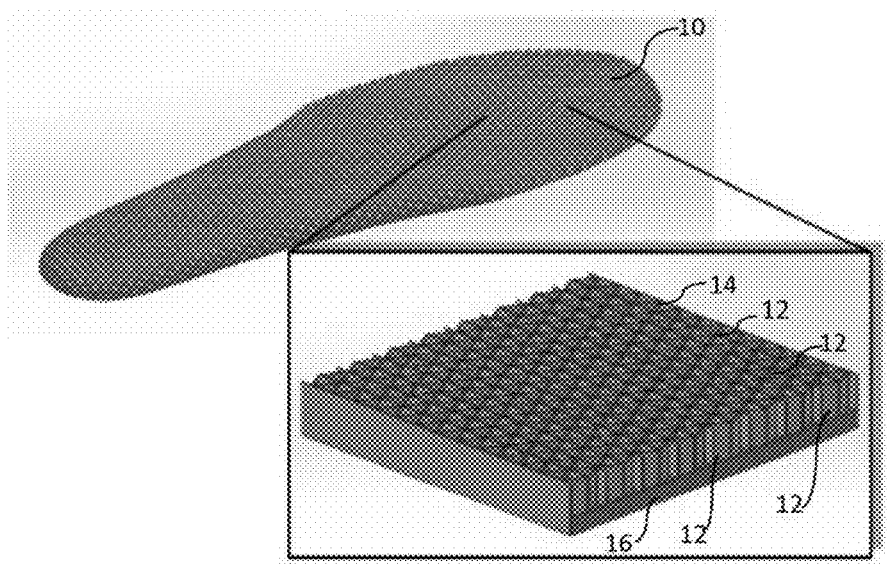
FIG. 2 illustrates one embodiment of an orthotic layer and includes an inset showing a portion of the layer cell geometry in higher definition.

FIG. 2 illustrates one embodiment of an orthotic layer 10. In this particular embodiment, the orthotic layer is a component of a full size insole orthotic, but it should be understood that the present disclosure is likewise directed to partial sole orthotics that are designed to extend across only a portion of the insole of a shoe. As utilized herein, the term "across" with regard to a foot orthotic is intended to refer to the dimensions of the orthotic that are generally parallel to the body and supporting structure, e.g., the insole of the shoe. Thus, "across" a foot orthotic would encompass dimensions from the heel section to the toe section and from side to side of the orthotic, and is intended to be differentiated from the height of the orthotic, e.g., the dimension of the orthotic from the support-contacting base surface to the body contacting top surface.

As illustrated in the inset of FIG. 2, the layer 10 includes a plurality of individual cells 12 across the layer 10. As shown, the cells 12 can be open at a first surface 14 (the upper surface in the orientation as shown in FIG. 2) and can be closed at the opposite surface 16, which can include a unitary substrate across the layer 10. This is not a requirement, however, and in some embodiments, the layer can include a unitary substrate on both the top and bottom of the layer such that the cells 12 are closed cells. In any case, the cells 12 of the layer 10 are organized in a predetermined pattern and in a single layer (i.e., a single non-overlapping stratum) across the orthotic layer 10 and as such are differentiated from an open or closed cellular foam, which includes a random orientation of a plurality of small overlapping cells.

Figure 3:
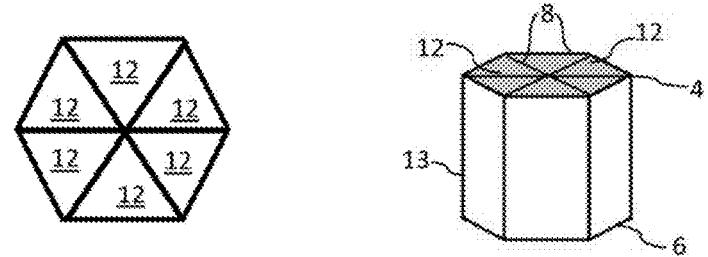
FIG. 3 presents a top view and a perspective view of one group of cells of the layer of FIG. 2.

FIG. 3 illustrates a group of individual cells 12 of the layer 10 of FIG. 2 in a top view (left) and a perspective view (right). As can be seen, in this embodiment, each cell 12 is triangular in cross section and is defined by the top 4, bottom 6 and surrounding wall 8 of the cell. A group of six individual cells 12 together form a hexagonal cylinder 13, with a plurality of the individual cells 12 and hexagonal cylinders 13 stretching across the layer 10 of FIG. 2.

Each cell 12 defines a void volume, which is the internal open area of the cell as bounded by the bottom 6, top 4, and surrounding side wall 8 of the cell 12, with the top 4 and bottom 6 of each cell being defined by a closed surface or alternatively, by a plane extending across the respective end of the surrounding wall.

The cross sectional shapes of the individual cells 12 of a layer are not particularly limited. The individual cells 12 of a layer can be triangular, as illustrated in FIG. 3 or any other desired shape. By way of example, and without limitation, FIGS. 4, 5, and 6 present top views of circular, hexagonal, and square cells, respectively. Moreover, combinations of cell cross sectional shapes and sizes across a layer are also encompassed herein. For instance FIG. 7 illustrates one embodiment of cell geometry including square cells of different sizes that would be considered practical for orthotics and associated anatomical considerations so as to affect skin/external surface pressures. While the size of the individual cells can vary, the cells 12 can generally have a perimeter of from about 1 mm to about 10 mm, with a height 13 ranging from about 1 mm to about 20 mm. For instance, the void volume of the individual cells 12 can vary from about 0.5 mm$^3$ (e.g., triangular perimeter of 1 mm and height 13 of 1 mm) to about 1000 mm$^3$ (e.g., triangular perimeter of 10 mm and height 13 of 20 mm). These ranges and dimensions, while practical for foot othotics, could be scaled to be practical for other anatomical locations, for example larger for the hip, head and buttox, and smaller for the elbow, hand and chin.

The hardness of a layer can be varied across the layer through variation of characteristics of the individual cells including void volume and/or formation materials. In general, the void volume of the individual cells can be controlled through variation in cell shape, wall thickness and/or cell height. For instance, FIG. 8, FIG. 9, and FIG. 10 illustrate top and side views of layer regions 110, 210, 310, respectively. In the embodiment of FIG. 8, the individual cells 112 are bounded between the top 104 and the bottom 106 by a surrounding wall 108 that is generally vertical from the top 104 to the bottom 106 of each cell and triangular in cross sectional shape. Thus, in this embodiment, the void volume of each cell 112 will simply be the volume of the triangular cylinder defined by the top 104, bottom 106, and surrounding wall 108 of each cell. As the void volume of each of the cells 112 is at the maximum, and the total void volume of the local region is defined only by the wall thickness of the surrounding walls 108, the hardness of the layer region illustrated in FIG. 8 can be relatively low.

Referring to FIG. 9, the individual cells 212 of the layer region 210 have a similar triangular cross sectional shape as the cells illustrated in FIG. 8, and the individual cells 212 are likewise grouped together to form a pattern of hexagonal cylinders across the layer region 210. But in the side view of region 210, it can be seen that the surrounding wall 208 is tapered between the bottom 206 and the top 204 of each cell. Thus, in this layer region 210, the void volume of the individual cells 212 (and thus the void volume of the entire region 210) will be smaller than that of the cells 112 and layer region 120 of FIG. 8. Assuming that the two layer regions 110, 210 are formed of the same material, the decreased void volume of the layer region 210 as compared to that of layer region 110 will lead to an increase in the overall hardness of the region 210.

In the embodiment of FIG. 10, the layer region 310 is similar to that of the other layer regions 110, 210, but the surrounding wall 308 of each cell 312 is tapered, and is tapered to a greater extent than is the surrounding wall 208 of the cells 212 of FIG. 9. As such the void volume of each of the cells 312 of the region 310 is smaller yet as compared to the cells 212 of the region 210 and the cells 112 of the region 110. Assuming that the layer region 310 is formed of the same material as the layer regions 210 and 110, the layer region 310 will exhibit an increase in the overall hardness as compared to the other two.

Thus, by decreasing the void volume of the cells in a select region of a layer, the overall hardness of that region will increase as compared to other regions with lower void volume cells. This approach can be utilized to fine tune the hardness characteristics across an entire layer. Moreover, due to the high formation control available in many formation schemes, the variation in hardness between adjacent regions can be very small. The development of a large number of different hardness regions across the layer can thus be utilized to develop a hardness gradient across the orthotic, which can improve comfort to the patient and pressure offloading characteristics in targeted area.

While tapering the surrounding wall of the individual cells may be a useful route to controlling the void volume of individual cells, it should be understood that the void volume control mechanism is not limited to this approach. Any suitable method for controlling the void volume of the individual cells can be utilized. For instance, in one embodiment, the surrounding wall thickness can be varied equally over the entire depth of the surrounding wall, rather than as a taper across the depth. In one embodiment, the surrounding wall thickness can be varied unequally over a portion of, or the entirety of the surrounding wall, either along the wall dimension 8 or height 13 (FIG. 3). This can include additions to or subtraction from a reference wall thicknesses, including the addition or subtraction of geometric shapes, lines, waves or otherwise, so as to reproducibly affect the resulting hardness of the shape through the alteration of the void geometry. This wall alteration can likewise include the subtraction of specific wall areas such that holes, pores or vents are created along the walls, thus affecting void volume. Similarly, the void volume can be controlled by varying the depth of the individual cells without modifying the surrounding wall thickness of the cells.

In conjunction with modification of the cell geometry across a layer, hardness across a layer can be controlled through control of the materials utilized to form the layer. For instance, polymeric compositions including one, two or more polymers of different shore hardness or elastic moduli may be combined in varying quantities in combination with variation in the cell geometry to provide varying hardness across the orthotic layer. By way of example, a first region can be formed of a first polymeric composition that includes a first polymer and a second region can be formed of a second polymeric composition that includes the first polymer and a second polymer in a blend. Alternatively, a second region may be formed of a polymeric composition that does not have a polymer in common with a first region. In such an embodiment, the layer can also include a third region between the first and second regions in which the polymer components of the compositions are gradually modified, e.g., the presence of the first polymer is gradually reduced and the presence of a second polymer is gradually increased in a transition region between the first region and the second region.

In general, the layer can be formed of a polymeric composition that includes one or more polymers optionally in conjunction with typical additives as are known in the art. As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

The preferred polymer for a layer can generally depend upon the targeted hardness range as well as the formation methods to be utilized in forming the layer. By way of example and without limitation, the layer may be constructed from thermoplastic polyolefin polymer, polyurethane, elastomer, etc. For example, a polyurethane that includes isocyanates and polyols at a desirable ratio to provide the desired hardness level in conjunction with pigments, stabilizer, etc. may be employed. Other materials such as thermoplastic polyethylene homopolymers or copolymers, ethylene vinyl acetate copolymers, crosslinked polyethylene copolymers, etc. can be utilized in forming a layer. While the layer can be formed of a foamed polymeric composition in one embodiment, this is not a requirement and in other embodiments, the layer may be formed of a non-foamed polymeric composition.

The hardness values of regions of a layer can vary as described. In one embodiment a layer can include Shore OO Hardness values of from about 20 to about 200 as determined according to ASTM D 2240-05, for instance by use of a materials testing system as is available from the Instron Corporation. For instance, a region of lower hardness in a layer can have a Shore OO Hardness of from about 30 to about 50, or about 35 to about 45 in some embodiments, another region of a layer can have a Shore OO Hardness of from about 75 to about 100, or from about 85 to about 95, and a harder region of a layer can have a Shore OO Hardness of from about 100 to about 200, for instance from about 110 to about 160 in some embodiments. Of course, a layer can optionally include a larger number of regions that can be designed to exhibit hardness gradients across the layer.

FIG. 11 is a photograph of an exemplary layer 410. As can be seen, the layer 410 includes a large number of individual cells 412 of a generally triangular cylinder shape and the individual cells are arranged across the layer 410 to form a plurality of hexagonal cylinders across the layer. In this particular embodiment, the layer cells are open at the upper surface as shown.

While the method of formation of the layer is not particularly limited, in one embodiment a layer can be formed according to an additive manufacturing process. This can be particularly beneficial in some embodiments as additive manufacturing methods can not only provide for precise control of material deposition in formation of a layer, but can also provide for local manufacturing, even in-house manufacturing at the point of care in some embodiments.

As utilized herein, the term additive manufacturing refers to a formation method in which a structure is formed according to a controlled, incremental deposition and/or solidification process. For instance, additive manufacturing can refer to 3D printing by use of e.g., extrusion deposition or powder deposition optionally in combination with chemical binding, thermal binding, photopolymerization, etc.; as well as lamination, stereolithography, casting, and so forth.

The main differences between additive manufacturing processes are the types of materials to be deposited and the way the materials are deposited and solidified. Some methods extrude materials including liquids (e.g., melts or gels) and extrudable solids (e.g., clays or ceramics) to produce a layer, followed by spontaneous or controlled curing of the extrudate in the desired pattern. Other processes deposit solids in the form of powders or thin films, followed by the application of energy and/or binders often in a focused pattern to join the deposited solids and form a single, solid structure having the desired shape. In some methods, successive layers are individually treated to solidify the deposited material prior to deposition of the succeeding layer, with each successive layer becoming adhered to the previous layer during the solidification process.

Additive manufacturing processes can differ from one another with regard to the composition and phase of the materials used to form individual layers as well as with regard to the method utilized to deposit and/or solidify the layer/structure. For instance, disclosed methods can be utilized with additive manufacturing processes that deposit the formation materials as a liquid as well as with additive manufacturing processes that deposit the formation materials in a solid phase.

In one embodiment, an additive manufacturing process can be used in which the formation material is extruded to form successive sub-layers of a layer. For instance, a liquid phase material can be deposited in the form of a gel or suitable highly viscous liquid that can be extruded in the desired pattern. For example, a polymer melt or solution can be deposited via extrusion in a desired pattern and the extrudate can then be cured through, e.g., a change in temperature (e.g., spontaneously upon deposition) or via crosslinking (e.g., a UV or otherwise actively initiated curing mechanism). Following, another layer or area of the extrudate can be applied, followed by cure, and so on to build the entire three dimensional structure. Alternatively, successive areas (e.g., layers) of the extrudate can be built up and the entire structure can be cured in a single process. For instance, successive areas of polymeric composition(s) can be deposited to form a green structure, and the entire structure can be cured in a single step.

Materials that can be deposited via extrusion can include, without limitation, thermoplastics (e.g., polyolefins, polystyrenes, polyvinyl chloride, elastomeric thermoplastics, polycarbonates, polyamides, etc.), silicone rubbers, and so forth. Extrusion techniques are often utilized with fused deposition modeling, in which the extrudate is deposited from a nozzle that can be moved in both the horizontal and vertical directions according to the control system. The desired structure can be manufactured by extruding successive beads or filaments of the extrudate to form the final product.

The formation material can alternatively be deposited in the form of a powder to form a single area (e.g., a layer or region), and select areas of the powder layer can then be cohered according to the desired pattern to solidify the powder in the desired pattern and form a single layer of the structure. Following, another area of the powder can be deposited, the solidification process can be repeated, and the entire object can be produced. Powder deposition techniques can be beneficial in some embodiments as the excess powder that is not solidified can surround and support the structure during formation. This support can provide for the formation of more complicated structures.

A powder of the desired formation material can be deposited in a layer generally on the order of about 1000 micrometers (μm) in thickness or less, about 500 μm in thickness or less, or about 100 μm in thickness or less. The powder grain size is not particularly limited, and can be, e.g., about 500 μm or less in average size, about 200 μm or less in average size, about 100 μm or less in average size, or about 50 μm in less in average size in some embodiments.

In other embodiments, such as stereolithography, the formation material can be a liquid, for instance a liquid held in a liquid bath, and the material can be solidified through exposure to a curing force, e.g., ultraviolet light, one area at a time according to a predetermined pattern. For instance, a formation stage can be submerged in the liquid formation material, and a pattern can be traced in the liquid by a suitable energy source to solidify a first area of the formation material. As the stage is lowered in the bath, subsequent areas of the formation material can be solidified to build the final form.

Once an individual area has been formed, deposited, or otherwise patterned, either through extrusion, powder deposition, or some other process, the solidification of the formation material in specific areas and adherence between individual areas can be carried out in any fashion. For instance, deposited materials may cohere spontaneously upon deposition, for instance in the case of a fused deposition method utilizing an extrusion deposition process (e.g., a polymeric melt). Alternatively, cohesion of the deposited material can be actively instigated or encouraged following deposition. For example, a binder material can be deposited on a layer of the formation material according to the desired pattern and can bind the formation material to a cohesive solid. For example, an inkjet printer can be used to deposit a binder on a previously formed layer. The binder can be, e.g., water, an acrylate binder, an epoxy, etc. as is known in the art and can include a dye or other additive as is known.

Selective cohering of the formation materials can be carried out by methods as are generally known such as through variation in local environmental conditions (e.g., temperature, pressure, etc.), through the focused addition of energy (e.g., laser or UV curing, melting, or sintering), and so forth.

Electron beam energy can also be utilized to solidify a formation material following deposition. Electron beam manufacturing fully melts a powder, e.g., a metal or metal alloy powder, following deposition and is generally utilized in forming a fully-dense structure with high strength characteristics.

Figure 12:
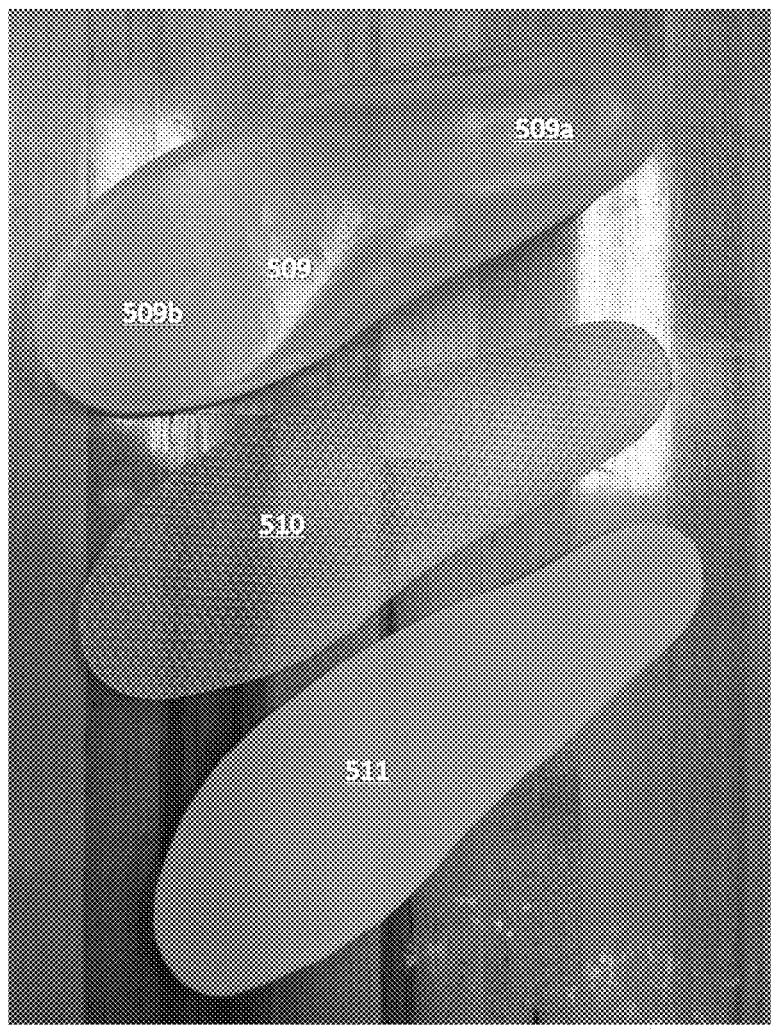
FIG. 12 is a photograph of a base layer, a cushion layer, and a top layer prior to combination to form a foot orthotic.

In one embodiment, an orthotic can include multiple layers. For example, FIG. 12 illustrates three different layers as may be included in a foot orthotic including a base layer 509, a cushion layer 510, and a top layer 511. One or more of the layers can be variable hardness layers as described herein. For instance, in one embodiment, at least the cushion layer 510 can be a variable hardness layer as described herein.

The base layer 509 can generally be formed of a non-foam polymeric composition. For example, the base layer can be formed from a non-foam elastomer such as the class of materials known as viscoelastic polymers or silicone gels, which can show high levels of damping when tested by dynamic mechanical analysis performed in the range of −50° C. to 100° C. As the mechanical properties of viscoelastic polymers can be more viscous than elastic, the base layer can exhibit a high degree of energy absorption. Suitable materials for a base layer 509 can include thermoset or thermoplastic elastomers (elastomeric materials), such as materials made from many polymeric families, including but not limited to styrene-olefin-rubber block copolymers, thermoplastic polyurethanes, thermoset polyurethanes, thermoplastic polyolefins, polyamides, polyureas, polyesters and other polymer materials that can reversibly soften as a function of temperature.

The material of the base layer can be selected in one embodiment to form a non-slip contact with the sole of a shoe, so as to better retain the foot orthotic in position without slipping.

The base layer 509 of a foot orthotic can also exhibit a variable hardness across the layer. For instance, the base layer 509 can vary in materials of formation across the layer, with a first region 509a of the base layer 509 being formed of a first polymeric composition and exhibiting a hardness, and a second region 509b of the base layer 509 being formed of a second polymeric composition and exhibit a second hardness. The polymeric compositions of different regions can vary from one another with regard to the presence or absence of one or more polymers in the composition as well as with regard to the presence or absence of one or more non-polymeric additives. In one embodiment, the relatively soft regions of a base layer can correspond to the locations of the relatively soft regions of a cushion layer with which it will be combined, but this is not a requirement of the foot orthotic.

The hardness value of a base layer 509 can generally vary from about Shore OO Hardness 75 to about Shore OO Hardness 200. For instance, a relatively soft region of a base layer 509 can have a Shore OO Harness of from about 75 to about 100, while a relatively hard region of a base layer 509 can have a Shore OO Hardness of from about 130 to about 150. Of course, multiple regions have hardness gradients can be developed across a base layer, if desired. For instance, in one embodiment a base layer can be formed according to an additive manufacturing process, and the material of formation can be varied across the base layer so as to vary the hardness across the layer in a desired fashion.

A foot orthotic can also include a top layer 511 that can be located on an upper surface of a cushion layer 510. A top layer 511 can be made from any suitable material such as fabric, leather, leatherboard, expanded vinyl foam, flocked vinyl film, coagulated polyurethane, latex foam on scrim, supported polyurethane foam, laminated polyurethane film or in-mold coatings such as polyurethane, styrene-butadiene-rubber, acrylonitrile-butadiene, acrylonitrile terpolymers and copolymers, vinyls, or other acrylics, as integral top covers. In In one embodiment, a top layer 511 can be made from a low friction fabric so that there is not a large amount of friction between the subject's foot and layer 511. This can help to retain the foot orthotic in the proper position within the shoe.

Desirable characteristics of a top layer 511 can include durability, stability and visual appearance. A top layer 511 can generally have good flexibility, as indicated by a low modulus in order to be easily moldable.

Figure 13:
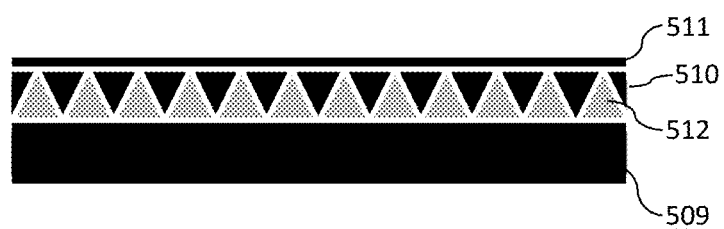
FIG. 13 illustrates a side view of a three-layer foot orthotic.
Figure 14:
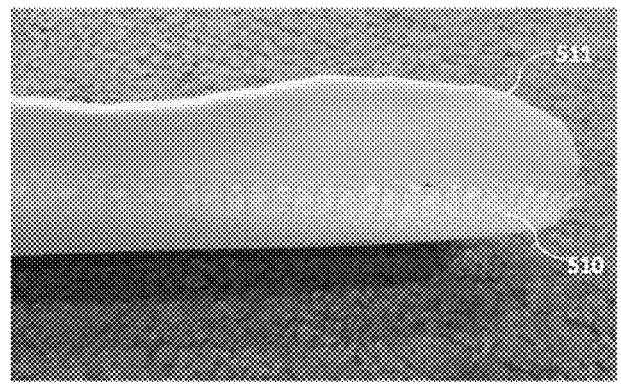
FIG. 14 illustrates a cushion layer and a top layer of a foot orthotic.

To form a foot orthotic, the various layers of the orthotic can be located adjacent to one another. For instance, FIG. 13 presents a cross sectional side view of a foot orthotic including a base layer 509, a cushion layer 510, and a top layer 511. As shown, in this embodiment the individual cells 512 of the cushion layer 510 are located such that the open surface of the cushion 510 faces the base layer 509. In this fashion, the cushion layer 510 can provide the desired softness in the local region, while still maintaining resilience and long life of the foot orthotic. FIG. 14 illustrates a cushion layer 510 and a top layer 511 aligned in such a fashion with the open cell surface facing away from the top layer 511. Depending upon the specific nature of the cushion layer and the relationship between the adjacent layers, however, in some embodiments it may be preferable to have the cushion layer arranged with open cell tops at the upper, foot-contacting side of the foot orthotic.

The multiple layers of a foot orthotic can be held adjacent to one another simply by the surrounding structure, e.g., a shoe, or can be adhered to one another by use of any suitable bonding technique such as melt bonding or adhesive bonding. In the case of melt bonding, care should be taken to maintain the desired geometric structure of the layers, however. Moreover, the use of adhesives should avoid the presence of excess adhesive within the cells of a layer, which could affect the desired hardness characteristics of a region.

Figure 15:
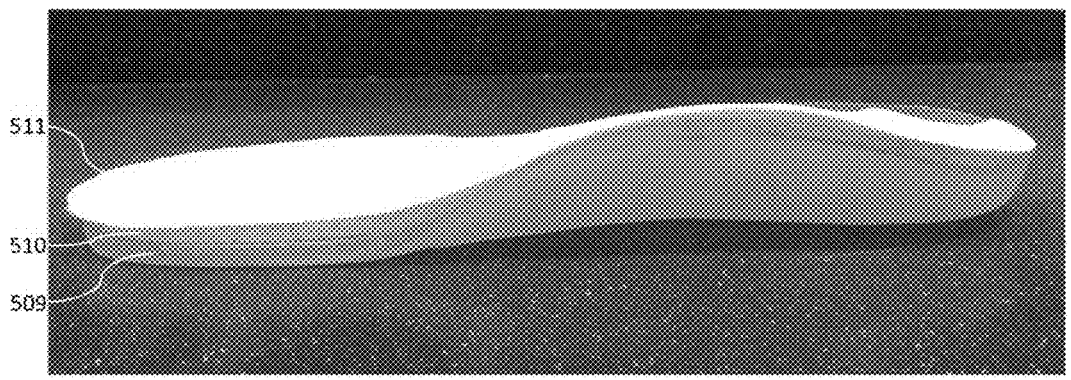
FIG. 15 illustrates a three-layer foot orthotic.

FIG. 15 illustrates a three-layer foot orthotic including a base layer 509, a cushion layer 510, and a top layer 511. As illustrated, the foot orthotic can be shaped to comfortably accommodate a subject's foot including arch support, heel support, toe support, etc. as are generally known in the art.

In one embodiment, the lower surface of a foot orthotic can be secured to the insole of a shoe by inherent tack properties of the materials used to form the lower surface of the base layer or by adding a tackifier to the insole or the base layer.

Figure 16:
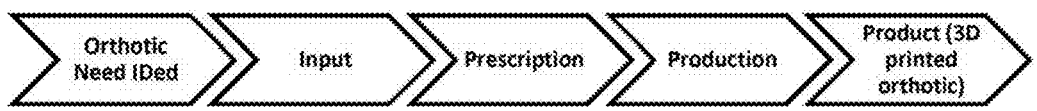
FIG. 16 presents a flow chart of a method of forming a foot orthotic.

In one embodiment, a custom-made foot orthotic can be provided for a subject. According to this embodiment, a custom-made orthotic can first be designed via clinical evaluation of the patient. For instance, and with reference to FIG. 16, following determination that an orthotic is needed for a patient, a variety of physical input data can be obtained. In one embodiment a reference insert orthotic can placed into a patient's shoe to obtain a reference topography and size. Clinical evaluation can be used to determine pressure points for the patient, for instance using pressure sensing technology as is known in the art such as, and without limitation, foot impressions, castings, or other 3D impressions of the patient's foot. Computer aided orthotic development or 3D scanners can also be utilized to provide the necessary input. For instance, pressure sensing technology as described in U.S. Pat. No. 9,020,626 to Specter, which is incorporated herein by reference, can be utilized in development of the foot orthotic.

A method may include scanning the foot against which the orthotic is to be positioned. A method may comprise extracting dimensions from the scanned body part to form a CAD image of the orthotic. Alternatively, the 3D data may be derived from an image and/or data set within a stock library. For example, an image of an orthotic may be selected from an image library, the orthotic selected being one that closely resembles an orthotic suitable for the shape of an intended user's foot and, when used for a medical application, suitable for treating a user's condition.

After the necessary input is obtained, software may be used to form an outline of an orthotic compatible with the scanned body part. In such embodiments, human intervention may also be used to provide expert knowledge and to check that the design orthotic is suitable.

This design information can be combined with clinical evaluation data such as patient weight, height, activity level, medical diagnosis (e.g., clubfoot, pressure ulcer, other abnormalities by plantar region, etc.), and desired orthotic use. Based on this study, a geometrically-desired durometer-map can then be designed for the patient that can provide an individualized orthotic prescription.

The orthotic can then be produced either in-house or through an external manufacturing source. For instance the cushion layer and the base layer can be manufactured via an additive manufacturing process in-house, and an orthotist/pedorthist can assess if the custom orthotic has achieved the desired outcomes of offloading (using pressure mapping) and fit.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. An orthotic layer that exhibits a variable hardness across the orthotic layer, the orthotic layer comprising an upper surface and a lower surface and a plurality of cells arranged in a predetermined pattern across the orthotic layer, wherein every cell of the plurality of cells extends between the upper surface and the lower surface and every cell of the plurality of cells is open at either the upper surface or the lower surface of the orthotic layer, the plurality of cells including a first portion of cells in a first region of the orthotic layer, each cell of the first portion of cells having a first void volume, the plurality of cells including a second portion of cells in a second region of the orthotic layer, each cell of the second portion of cells having a second void volume, the first region having a first hardness and the second region having a second, different hardness as determined according to ASTM D 2240-05.

2. The orthotic layer of claim 1, wherein the orthotic layer is a layer of a foot orthotic.

3. The orthotic layer of claim 2, wherein the orthotic layer is a cushion layer.

4. The orthotic layer of claim 1, wherein every cell of the plurality of cells has an identical cross sectional shape to every other cell of the plurality of cells.

5. The orthotic layer of claim 1, wherein the plurality of cells includes cells of different cross sectional shapes and/or sizes.

6. The orthotic layer of claim 1, wherein every cell of the plurality of cells has a perimeter of from about 1 mm to about 10 mm.

7. The orthotic layer of claim 1, wherein every cell of the plurality of cells includes a surrounding wall, wherein a taper of the surrounding wall of each cell of the first portion of cells is different from a taper of the surrounding wall of each cell of the second portion of cells.

8. The orthotic layer of claim 1, wherein the composition of formation of the first portion of cells differs from the composition of formation of the second portion of cells.

9. The orthotic layer of claim 1, wherein the plurality of cells extend across the entire orthotic layer.

10. The orthotic layer of claim 1, wherein the orthotic layer is a layer of a knee orthotic, an ankle orthotic, a hip orthotic, a spinal orthotic, a wrist orthotic, an elbow orthotic, a shoulder orthotic, a hand/palm/grip cushion system, a head/helmet cushion system, an elbow cushion system, or a hip/buttocks cushion systems.

11. An orthotic comprising:
a base layer;
a cushion layer adjacent to the base layer, the cushion layer comprising an upper surface and a lower surface and plurality of cells arranged in a predetermined pattern across the cushion layer, the lower surface of the cushion layer being adjacent to an upper surface of the base layer, wherein every cell of the plurality of cells extends between the upper surface and the lower surface of the cushion layer and every cell of the plurality of cells is open at either the lower surface of the cushion layer or the upper surface of the cushion layer, the plurality of cells including a first portion of cells in a first region of the cushion layer, each cell of the first portion of cells having a first void volume, the plurality of cells including a second portion of cells in a second region of the cushion layer, each cell of the second portion of cells having a second void volume, the first region having a first hardness and the second region having a second, different hardness as determined according to ASTM D 2240-05; and optionally
a top layer adjacent to the cushion layer, the upper surface of the cushion layer being adjacent to a lower surface of the top layer, when present: wherein
the base layer, the cushion layer, and the top layer when present are not adhered to one another.

12. The orthotic of claim 11, wherein the orthotic is a foot orthotic.

13. The orthotic of claim 11, wherein every cell of the plurality of cells has a perimeter of from about 1 mm to about 10 mm.

14. The orthotic of claim 11, wherein every cell of the plurality of cells includes a surrounding wall, wherein a taper of the surrounding wall of each cell of the first portion of cells is different from a taper of the surrounding wall of each cell of the second portion of cells.

15. The orthotic of claim 11, wherein the composition of formation of the first portion of cells differs from the composition of formation of the second portion of cells.

16. The orthotic of claim 11, wherein the base layer exhibits a variable hardness across the base layer.

17. The orthotic of claim 11, wherein the plurality of cells extend across the entire cushion layer.

18. The orthotic of claim 11, wherein the orthotic is a knee orthotic, an ankle orthotic, a hip orthotic, a spinal orthotic, a wrist orthotic, an elbow orthotic, a shoulder orthotic, a hand/palm/grip cushion system, a head/helmet cushion system, an elbow cushion system, or a hip/buttocks cushion systems.

* * * * *